United States Patent
Hedberg et al.

(10) Patent No.: US 8,359,095 B2
(45) Date of Patent: Jan. 22, 2013

(54) MEDICAL SYSTEM AND A METHOD FOR DETERMINING SETTINGS OF AN IMPLANTABLE DEVICE

(75) Inventors: Sven-Erik Hedberg, Kungsängen (SE); Patrik Malmberg, Stockholm (SE); Leif Lychou, Spånga (SE); Jürgen Kerstna, Hässelby (SE)

(73) Assignee: Pacesetter, Inc., Sylmar, CA (US)

( * ) Notice: Subject to any disclaimer, the term of this patent is extended or adjusted under 35 U.S.C. 154(b) by 703 days.

(21) Appl. No.: 12/442,742

(22) PCT Filed: Sep. 25, 2006

(86) PCT No.: PCT/SE2006/001081
§ 371 (c)(1),
(2), (4) Date: Dec. 19, 2009

(87) PCT Pub. No.: WO2008/039110
PCT Pub. Date: Apr. 3, 2008

(65) Prior Publication Data
US 2010/0106212 A1      Apr. 29, 2010

(51) Int. Cl.
*A61N 1/365* (2006.01)
*A61N 1/372* (2006.01)
(52) U.S. Cl. .............................. 607/17; 600/520; 607/28
(58) Field of Classification Search .................. 600/520; 607/17
See application file for complete search history.

(56) References Cited

U.S. PATENT DOCUMENTS

| | | | |
|---|---|---|---|
| 4,886,064 A | 12/1989 | Strandberg | |
| 5,044,365 A | 9/1991 | Webb et al. | |
| 5,063,927 A | 11/1991 | Webb et al. | |
| 5,372,607 A | 12/1994 | Stone et al. | |
| 6,839,593 B1 * | 1/2005 | Sun et al. | 607/17 |
| 6,975,904 B1 * | 12/2005 | Sloman | 607/28 |
| 2003/0204147 A1 * | 10/2003 | Condie et al. | 600/520 |
| 2004/0220636 A1 | 11/2004 | Burnes | |
| 2005/0043895 A1 | 2/2005 | Schechter | |
| 2005/0234517 A1 | 10/2005 | Braunschweig et al. | |

OTHER PUBLICATIONS

"Treadmill Assessment of an Activity-Modulated Pacemaker: The Importance of Individual Programming," McAlister et al, PACE, vol. 12 (1989) pp. 486-501.

* cited by examiner

*Primary Examiner* — Carl H Layno
*Assistant Examiner* — Erin Piateski (57) ABSTRACT

In a medical system and a method for operating such a system, the system includes an implantable medical device of a patient, a programmer device, and an extracorporeal stress equipment adapted to exert a physiological stress on the patient, for automatically determining settings of a sensor for sensing a physiological parameter of the patient or for automatically determining a pacing setting of the device over a broad range of workloads of the equipment. The ingoing units and/or devices of the medical system, i.e. the implantable medical device of the patient, the programmer device, and the extracorporeal stress equipment, communicate bi-directionally with each other and form a closed loop.

52 Claims, 8 Drawing Sheets

MEDICAL SYSTEM AND A METHOD FOR DETERMINING SETTINGS OF AN IMPLANTABLE DEVICE

BACKGROUND OF THE INVENTION

1. Field of the Invention

The present invention generally relates to cardiac pacing systems and, in particular, to methods and medical systems including implantable medical devices, for automatic characterization of sensors of such implantable medical devices and automatic evaluation of settings, e.g. pacing settings such as VV-delays, of such devices.

2. Description of the Prior Art

Medical devices are implanted in human bodies for e.g. monitoring physiological conditions or treating diseases. One particular example of implantable medical devices is a cardiac rhythm management device including pacemakers and defibrillators implanted in a patient to treat irregular or other abnormal cardiac rhythms by delivering electrical pulses to the patient's heart. Pacemakers are often used to treat patients with bradyarrythmias, that is, hearts that beat too slow or irregularly. Defibrillators are capable of delivering higher energy electrical stimuli to the heart and are often used to treat patients with tachyarrythmias, that is, hearts that beat too quickly.

Such implantable medical devices comprises a number of sensors which are used to sense different physiological parameters of the patient, and in particular of the patient's heart, in order to deliver an accurate and reliable stimuli of the heart with respect to timing, amplitude etc. For example, sensors for determining an activity level of the patient, e.g. an accelerometer, sensors for determining a breathing rate of the patient are often included in such implantable medical devices. In order to obtain a reliable and correct operation of the implantable device, the characteristics and settings of the sensors must be determined in an accurate way.

Today, the normal procedure for determining the sensor characteristics and/or settings, e.g. of an activity sensor of an implanted medical device, is to start the collection of the sensor data via a programmer. The patient is then asked to lie down during a period of time and to perform a walk during a second period of time. In this way, sensor data is registered at two different activity levels; namely at rest and at normal walking.

However, this mainly manual procedure for sensor characterization is associated with a number of drawbacks. For example, the sensor is characterized over a rather limited patient activity level range which may lead to an impaired function of the device due to a non-complete or limited sensor is characterization. Furthermore, it may be difficult for the operator, e.g. the physician, conducting the patient test session to obtain reliable and reproducible results from the test, for example, due to the fact that the exerted workload during the walking is subjective for the patient and the actual workload is difficult to estimate.

A similar procedure is also conducted when setting up or adjusting pacing settings of an implanted medical device, e.g. setting up or adjusting a V-V timing of a pacemaker after an implantation. In this case, the physician and/or nurse measure the cardiac output and adjusts the V-V timing manually and this is repeated until satisfying results are obtained. This procedure is in some cases also combined with activity level measurements, i.e. the patient is asked to lie down during a period of time and to perform a walk during a second period of time. This manual procedure for setting up or adjusting the pacing settings of an implanted device, such as a pacemaker, may, apart from being time consuming, lead to unreliable results, for example, due to the fact that the cardiac output has to be interpreted and connected to a new V-V delay.

Thus, there is a need of an improved and automatized procedure for characterization of rate-responsive sensors of implantable medical devices, such as pacemakers, and for an improved and automatic procedure for evaluation and optimizing of pacing settings of implantable medical devices, such as pacemakers.

United States Patent Application Publication No. 2004/0220636 discloses a system in which an IMD (Implantable Medical Device) programming device receives hemodynamic data from a hemodynamic measurement device (for example an external device) and programs one or more pacing parameters of the IMD as a function of the received pacing data. The IMD programming device is telemetrically linked to the IMD and may read, write, or store, for example, pacing parameters of the IMD to the IMD and/or to the IMD programming device. The hemodynamic measurement device monitors the patient and generates updated hemodynamic data and the programmer may set or adjust the pacing parameters of the IMD as a function of the updated hemodynamic data. However, this system requires that a physician or nurse conducts the test and instructs the patient, for example, in case of determining sensor characteristics at different activity levels, to lie down and to walk during certain periods of time. Accordingly, the system according to United States Patent Application Publication No. 2004/0220636 does not solve all the problems associated with the prior art procedures.

Hence, there remains a need within the art of an improved and automatized procedure for characterization of rate-responsive sensors of implantable medical devices, such as pacemakers, and for an improved and automatic procedure for evaluation and optimizing of pacing settings of implantable medical devices, such as pacemakers.

SUMMARY OF THE INVENTION

Thus, an object of the present invention is to provide methods and medical systems including implantable medical devices such as pacemakers for automatic characterization of sensors of such devices and automatic evaluation of settings, e.g. pacing settings such as VV-delay settings or AV-delay settings, of such devices.

Another object of the present invention is to provide an improved and automatized procedure and medical system for characterization of rate-responsive sensors of implantable medical devices, such as pacemakers, and for an improved and automatic evaluation and optimizing of pacing settings of implantable medical devices, such as pacemakers that are capable of delivering reliable and accurate results.

A further object of the present invention is to provide an improved and automatized procedure and medical system for characterization of rate-responsive sensors of implantable medical devices, such as pacemakers, and for an improved and automatic evaluation and optimizing of pacing settings of implantable medical devices, such as pacemakers, for a broad range of activity levels.

Yet another object of the present invention is to provide an improved method and system for automatically evaluating and optimizing pacing settings of an implantable medical device, such as pacemakers, for a broad range of activity levels.

In the context of this application, the term "hemodynamic parameter" refers to a parameter that can be measured, sensed or derived, for example, cardiac output, stroke volume, ejection fraction, blood pressure that reflects or relates to actual hemodynamic function.

For the purpose of clarification, the term "cardiogenic impedance" or "cardiac impedance" is defined as an impedance or resistance variation that origins from cardiac contractions, or in other words, an impedance of tissues measured between at least one electrode located within or at the heart and one or more electrodes located within, at or outside the heart.

According to an aspect of the present invention, there is provided a medical system for determining settings of an implantable medical device of the system, which device includes a controller or controlling circuit, a pulse generator adapted to produce cardiac stimulating pacing pulses and a communication unit. The system further has a programmer device including a control unit and a communication unit and at least one extracorporeal stress equipment adapted to, during use of/by the patient, exert a physiological stress on the patient, the equipment including a communication unit and a control device adapted to control the stress, wherein the extracorporeal stress equipment is adapted to, during operation, exert a physiological stress on a patient according to predetermined stress equipment workload settings. The programmer is adapted to downlink instructions to start a patient test session and to initiate an automatic setting determination procedure including starting an operation of the stress equipment, the implantable medical device comprises at least one sensor adapted to sense at least one sensor signal associated with a physiological parameter of the patient, wherein the is controlling circuit is adapted to obtain at least one sensor value using the sensor signal for each workload level of the stress equipment workload settings during the determination procedure, and the controlling circuit of the implantable medical device is adapted to determine the settings and/or characteristics of the at least one sensor for each workload level using the obtained sensor values.

According to a second aspect of the present invention, there is provided a medical system for optimizing pacing settings of an implantable medical device of the system, which device includes a controller or controlling circuit, a pulse generator adapted to produce cardiac stimulating pacing pulses and a communication unit. The system further has a programmer device including a control unit and a communication unit and at least one extracorporeal stress equipment adapted to, during use of/by the patient, exert a physiological stress on the patient, the equipment including a communication unit and a control device adapted to control the stress, wherein: the extracorporeal stress equipment is adapted to, during operation, exert a physiological stress on a patient according to predetermined stress equipment workload settings; the programmer is adapted to downlink instructions to start a patient test session and to initiate an automatic setting determination procedure including starting an operation of the stress equipment; a circuit for obtaining a hemodynamical parameter of the heart of the patient during successive cardiac cycles for each workload level of the stress equipment workload settings, and an evaluation circuit adapted to evaluate the at least one hemodynamical parameter, and the workload data for each workload level of the stress equipment workload settings; and wherein the controlling circuit is adapted to iteratively control a delivery of the so pacing pulses based on the evaluation and to determine optimal pacing settings for each workload level of the stress equipment workload settings.

According to a third aspect of the present invention, there is provided a method for determining settings of an implantable medical device in a medical system, the device including a pulse generator adapted to produce cardiac stimulating pacing pulses and a communication unit, wherein the system further comprises a programmer device including a control unit and a communication unit and at least one extracorporeal stress equipment adapted to, during use of/by the patient, exert a physiological stress on the patient according to an applied workload, the equipment including a communication unit and a control device adapted to control the applied workload. The method includes the steps of: starting a patient test session; initiating an automatic setting determination procedure comprising the steps of: starting an operation of the stress equipment, wherein the stress equipment, during operation, exerts a physiological stress on the patient according to predetermined stress equipment workload settings; sensing at least one sensor signal associated with a physiological parameter of the patient for each workload level of the stress equipment workload settings; obtaining at least one sensor value using the sensor signal; and determining the settings and/or characteristics of the at least one sensor for each workload level using the obtained sensor values.

According to a fourth aspect of the present invention, there is provided a method for optimizing pacing settings of an implantable medical device in a medical system, the device including a pulse generator adapted to produce cardiac stimulating pacing pulses and a communication unit, wherein the system further has a programmer device including a control unit and a communication unit and at least one extracorporeal stress equipment adapted to, during use of/by the patient, exert a physiological stress on the patient according to an applied workload, the equipment including a communication unit and a control device adapted to control the applied workload, the method comprising the steps of: starting a patient test session; initiating an automatic setting determination procedure comprising the steps of: starting an operation of the stress equipment, wherein the stress equipment, during the operation, exerts a physiological stress on the patient according to predetermined stress equipment workload settings; obtaining at least one hemodynamical parameter of the heart of the patient during successive cardiac cycles for each workload level of the stress equipment workload settings; obtaining is workload data including a currently applied workload level; evaluating the at least one hemodynamical parameter, the sensor signal value and the workload data; iteratively controlling a delivery of the pacing pulses based on the evaluation; and determining optimal pacing settings for each workload level of the stress equipment workload settings.

According to a fifth aspect of the present invention, there is provided a computer program product, which when executed on a computer, performs steps in accordance with the second and third aspects of the present invention.

According to a further aspect of the present invention, there is provided a computer readable medium comprising instructions for bringing a computer to perform steps of methods according to the third and fourth aspects of the present invention.

Thus, the present invention is based on idea of interconnecting at least one implantable medical device implanted in a patient, at least one programmer workstation, and at least one extracorporeal stress equipment adapted to exert a physiological stress on the patient in a medical system for automatically determining settings of a sensor for sensing a physiological parameter of the patient or for automatically determining a pacing setting of the device over a broad range of workloads of the equipment. The units and/or devices of the medical system, i.e. the implantable medical device of a patient, the programmer device, and the extracorporeal stress equipment, may communicate bi-directionally with each other and form a closed loop during, for example, the patient test session and the automatic setting determination procedure for automatically determining settings of a sensor for sensing a physiological parameter of the patient or automatically determining a pacing setting of the device over a broad range of workloads of the equipment and, hence, for a broad range of exertion levels of the patient. In particular, the extracorporeal stress equipment may be controlled by the implantable device or the programmer during the patient test session, wherein a workload of the stress equipment is adjusted in accordance with a predetermined workload setting such that the patient is exerted for different levels of stress.

This invention provides several advantages in comparison with the prior art. For example, a sensor can be characterized over a broad spectrum of patient stress levels. Thereby, the sensor function can be improved. Furthermore, it is possible for the physician conducting the patient test session to obtain reliable and reproducible results from the test, for example, due to the fact that the applied workload during the different workload settings can be set accurately by means of the stress equipment. Furthermore, the procedure for setting up or adjusting pacing settings of an implanted medical device, e.g. setting up or adjusting a V-V timing of a pacemaker after an implantation, can be done more efficiently since the optimization is performed automatically at different activity levels of the patient. Thus, the physician and/or nurse do not have to measure the cardiac output, adjust the V-V timing manually and repeat this until satisfying results are obtained. In addition, the pacing settings can be optimized over a broad range of patient stress level in an efficient and reliable manner with respect to hemodynamical function.

According to an embodiment of the present invention, the at least one sensor is an activity level sensor adapted to sense an activity level of the patient. There are a number of other physiological or hemodynamical parameters of the patient that may be used, for example, as an alternative or complement to the activity level including, without limitation, heart rate, breath rate, posture of the patient, blood temperature, etc. By using an activity sensor, a reliable and accurate measure of the extertion of the patient can be determined and, thus, the reliability and accuracy of, for example, the setting determination can be improved.

In a further embodiment, the implantable medical device further includes a memory circuit adapted to store the settings and/or characteristics of the at least one sensor value for each workload level. Accordingly, a complete sensor characterization may be stored, i.e. sensor signal value vs. stress equipment setting.

According to an embodiment of the present invention, the communication circuits, devices or units of the devices of the system, e.g. the programmer, the implantable medical device and the stress equipment, is RF telemetry circuits, devices, or units, which may be adapted for e.g. inductive telemetry or UHF telemetry.

In embodiments, a communication link between the programmer, the implantable medical device and the stress equipment is established, wherein two-way communications are enabled between the programmer, the implantable medical device and the stress equipment, respectively. Thus, the programmer may downlink data to the implantable medical device and data may be transferred uplink to the programmer from the implantable medical device. The two-way communication between the devices of the system can be realized by means of a number of different technologies including short-range communication links including BLUETOOTH, and IEEE 802.11b, or other types of short range wireless connections such as Infrared. Another alternative is using, for example, USB connections. Further, the devices of the system may communicate wirelessly with each other using RF-technology. The devices of the medical system may communicate with each other in a network forming a part of a wireless LAN ("Local Area Network"). For a given communication method, a multitude of standard and/or proprietary communication protocols may be used. For example, and without limitation, wireless (e.g. radio frequency pulse coding, spread spectrum frequency hopping, time-hopping, etc.) and other communication protocols (e.g. SMTP, FTP, TCP/IP) may be used. Other proprietary methods and protocols may also be used. Furthermore, combination of two or more of the communication methods and protocols may also be used.

In one embodiment, the programmer is adapted to, upon receiving a patient test session initiation command, to establish the communication link. Further, the programmer is adapted to, upon after having established the communication link to the implantable medical device, send a command initiating the automatic determination procedure to the implantable medical device. However, master device and slave device in the medical system according to the present invention may vary during a session.

According to another embodiment, the controlling circuit of the implantable medical device is adapted to obtain a list of stress equipment workload settings comprising a predetermined number of different workload levels; and wherein the controlling circuit is adapted to send running instructions to the extracorporeal stress equipment instructing the extracorporeal stress equipment to operate according to the stress equipment workload settings of the list. The list may be stored in the memory circuit of the implantable medical device or in the programmer. Alternatively, the programmer may be connected to a communication network and the list can be obtained from a database connected to the network or a computer connected to the network, which may be, for example, a LAN ("Local Area Network") or a WAN ("Wide Area Network"). The programmer may be connected to the communication network via a network such as Internet.

In yet another embodiment of the present invention, the implantable medical device further comprises a signal processing unit adapted to process the at least one sensor signal from at least one sensor of the implantable device, which signal processing unit is adapted to start a signal processing procedure of the sensor signal a predetermined period of time after an adjustment of workload according to the workload settings. Further, the signal processing circuit may be adapted to perform an averaging process of the sensor signal during the signal processing procedure. Alternatively or in addition, the signal processing circuit may be adapted to perform a filtering process of the obtained signals.

In yet another embodiment of the present invention, the circuit for obtaining a hemodynamical parameter comprises a circuit for measuring an impedance of tissues between right and left side of the heart for successive cardiac cycles; a circuit for measuring a heart rate of the patient; and wherein the circuit for obtaining a hemodynamical parameter is adapted to determine a relative cardiac output (CO) based on the measured impedance and the measured heart rate for successive cardiac cycles. Of course, as the skilled person within the art realizes, there are other hemodynamical parameters that can be measured, sensed or derived, for example, stroke volume, ejection fraction, heart sounds, blood pressure and used as metric of the hemodynamic function of the heart during the optimization procedure.

In a further embodiment of the present invention, the controlling circuit of the implantable medical device is adapted to: a) select an initial workload setting of the predetermined stress equipment workload settings; b) operate the stress equipment according to the selected workload setting; c) iteratively control the delivery of the pacing pulses based on the evaluation; d) determine optimal pacing settings for the initial workload level; e) store the optimal pacing setting and corresponding activity level for the initial workload level in the memory circuit of the implantable medical device; f) repeat steps b)-e) for each workload level of the stress equipment workload setting; and g) store a matrix of pacing settings and corresponding activity levels in the memory circuit.

According to embodiment, the pacing settings are VV-delay settings, but in alternative embodiments, the settings may be, for example, AV-delay settings.

The system according to the present invention may also comprise external diagnostic equipment, for example, an ultra sound machine connected to the patient. The ultra sound machine is adapted to communicate with the programmer and/or the implantable medical device and/or the stress equipment. For example, the programmer may control the ultra sound machine and the measurements results from the ultra sound machine can be used in the automatic setting determination procedure to characterizing a sensor and/or the optimization of pacing settings such as VV-delay or AV-delay settings can be performed using the measurements from the ultra sound machine. As the skilled man realize, there are a number of alternative or complementing device that can be used, for example, a breath monitoring device may be connected to the patient to measure or sense, for example, a composition of the expiration air of the patient.

According to another embodiment of the present invention, the condition of the patient undergoing the patient test session at the stress equipment is monitored or supervised. In one embodiment, the cardiac output (CO) and the patient activity levels are monitored or observed. In case of worsening of the condition, e.g. if the cardiac output is found to exceed or fall below predetermined limits, the workload of the stress equipment may be reduced. Thereby, the safety of the patient can be enhanced during the test sessions.

As realized by the person skilled in the art, steps of the methods of the present invention, as well as preferred embodiment thereof, are suitable to realize as a computer program or a computer readable medium.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

DESCRIPTION OF THE PREFERRED EMBODIMENTS

In the following, the present invention will be discussed in the context of a medical system comprising at least an implantable bi-ventricular pacemaker, an external or extracorporeal programmer workstation and an extracorporeal stress equipment. However, the present invention may also be implemented in system including other implantable devices such as a CRT (Cardiac Resynchronization Therapy) device, or an ICD (Implantable Cardioverter Defibrillator). Furthermore, the system may also include other devices, units or equipment such as, for example, an ultrasound machine.

Figure 1A:
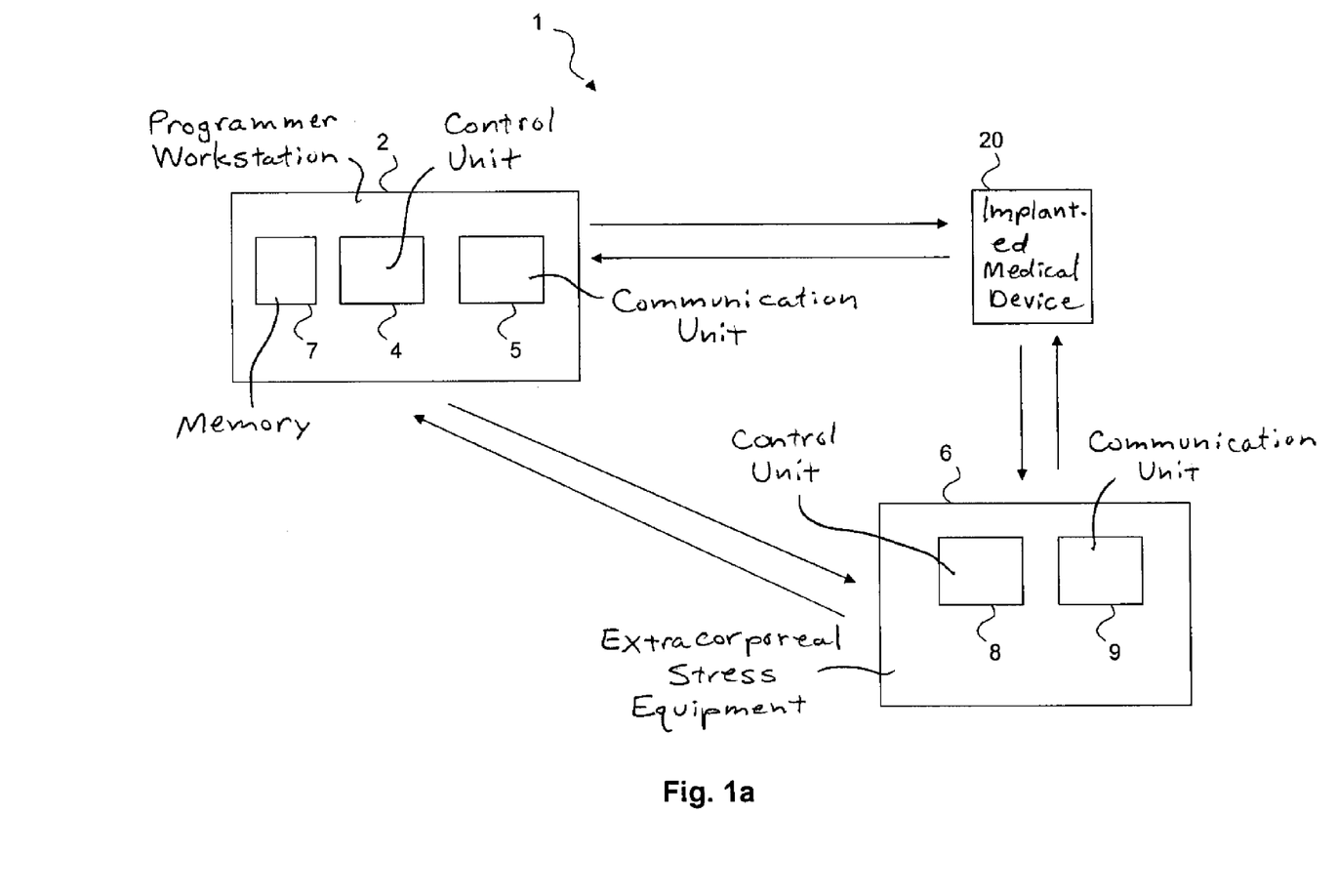
FIG. 1a schematically shows a medical system in accordance with an embodiment of the present invention.
Figure 1B:
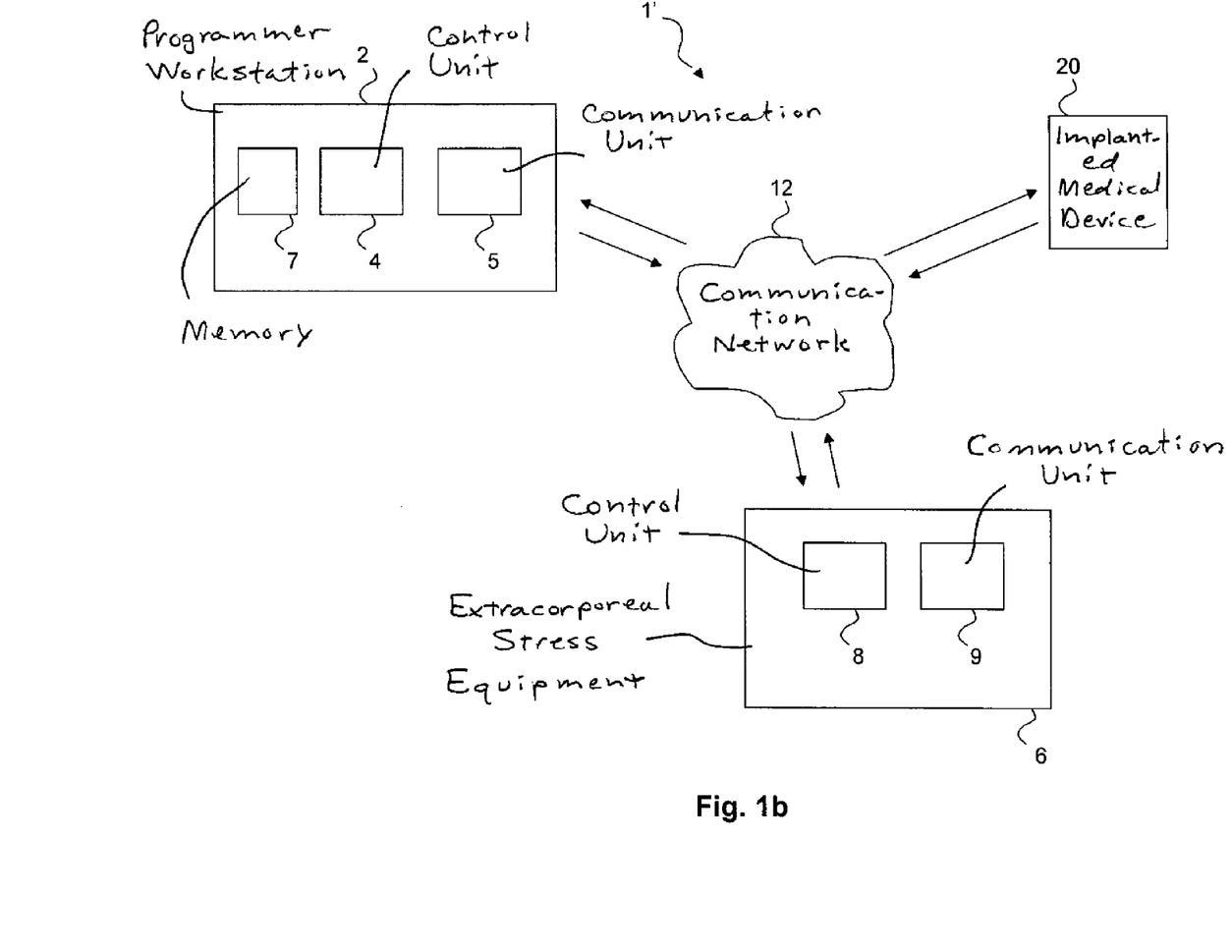
FIG. 1b schematically shows a medical system in accordance with another embodiment of the present invention.

With reference first to FIGS. 1a and 1b, embodiments of the medical system of the present invention will be described. In one embodiment of the present invention shown in FIG. 1a, the medical system 1 includes a programmer workstation 2, an implanted medical device 20 (which will be described in more detail with reference to FIGS. 2a and 2b) implanted in a patient (not shown) and extracorporeal stress equipment 6, for example, a treadmill. The programmer 2 includes a control unit 4 and a communication unit 5, i.e. an RF telemetry circuitry for providing bi-directional RF communications with, for example, the implanted medical device 20 and/or the stress equipment 6. The programmer 2 may downlink data, commands or instructions to the implanted medical device 20 and/or the stress equipment 6 and may receive data, commands or instructions uplink from the implanted medical device 20 and/or the stress equipment 6.

Further, the programmer 2 has a memory 7 for storing, for example, predetermined stress equipment workload settings for different patients, a display unit or monitor, (not shown) for presenting information for a user by means of a graphical user interface (GUI), and input devices (not shown), for example, a keyboard and a mouse, which enable a user to, for example, input information and commands such as a command for starting or initiating a patient test session. The stress equipment 6 has a control unit 8 adapted to, for example, control a workload of the equipment for, during use of a patient, exerting a physiological stress on the patient or starting an operation of the equipment, and a communication unit 9, i.e. an RF telemetry circuitry for providing bi-directional RF communications with, for example, the implanted medical device 20 and/or the programmer 2. The operations of the stress equipment 6 may be controlled, via the control unit 8 of the stress equipment, by the programmer 2 or the implantable medical device 20, for example, the operations during a patient test session for characterizing or determining the settings of a sensor of an implanted medical device 20 or determining or optimizing pacing settings of the implanted medical device 20.

The programmer 2, the implantable medical device 20 and the stress equipment 6 or the medical system 1 may be interconnected in a telemetry communication system which allows two-way communication between the units or devices of the medical system 1. As the skilled person realizes, the two-way communication between the devices of the system can be implemented by means of a number of different technologies including short range communication links including BLUETOOTH, and IEEE 802.11b, or other types of short-range wireless connections such as Infrared. Further, the devices of the system may communicate wirelessly with each other using RF-technology. Moreover, the devices of the medical system may communicate with each other in a network forming a part of a wireless LAN ("Local Area Network").

The programmer 2, the implantable medical device 20 and the stress equipment 6 of the medical system 1' may also communicate with each other via a communication network 12, such as, the internet or a wireless RF communication network 12, see FIG. 1b.

For a given communication method, a multitude of standard and/or proprietary communication protocols may be used. For example, and without limitation, wireless (e.g. radio frequency pulse coding, spread spectrum frequency hopping, time-hopping, etc.) and other communication protocols (e.g. SMTP, FTP, TCP/IP) may be used. Other proprietary methods and protocols may also be used. Further, combination of two or more of the communication methods and protocols may also be used.

The bi-directional communication between the implantable medical device 20 and the external stress equipment 6 may be a virtual bi-directional communication, i.e. the programmer 2 acts as an intermediary device between the implantable medical device 20 and the stress equipment 6.

In another embodiment of the present invention, the medical system also has external diagnostic equipment, for example, an ultrasound machine connected to the patient. Thereby, the automatic setting determination procedure to characterizing a sensor and/or the optimization of pacing settings such as VV-delay or AV-delay settings can be performed using the measurements from the ultra sound machine.

Figure 2A:
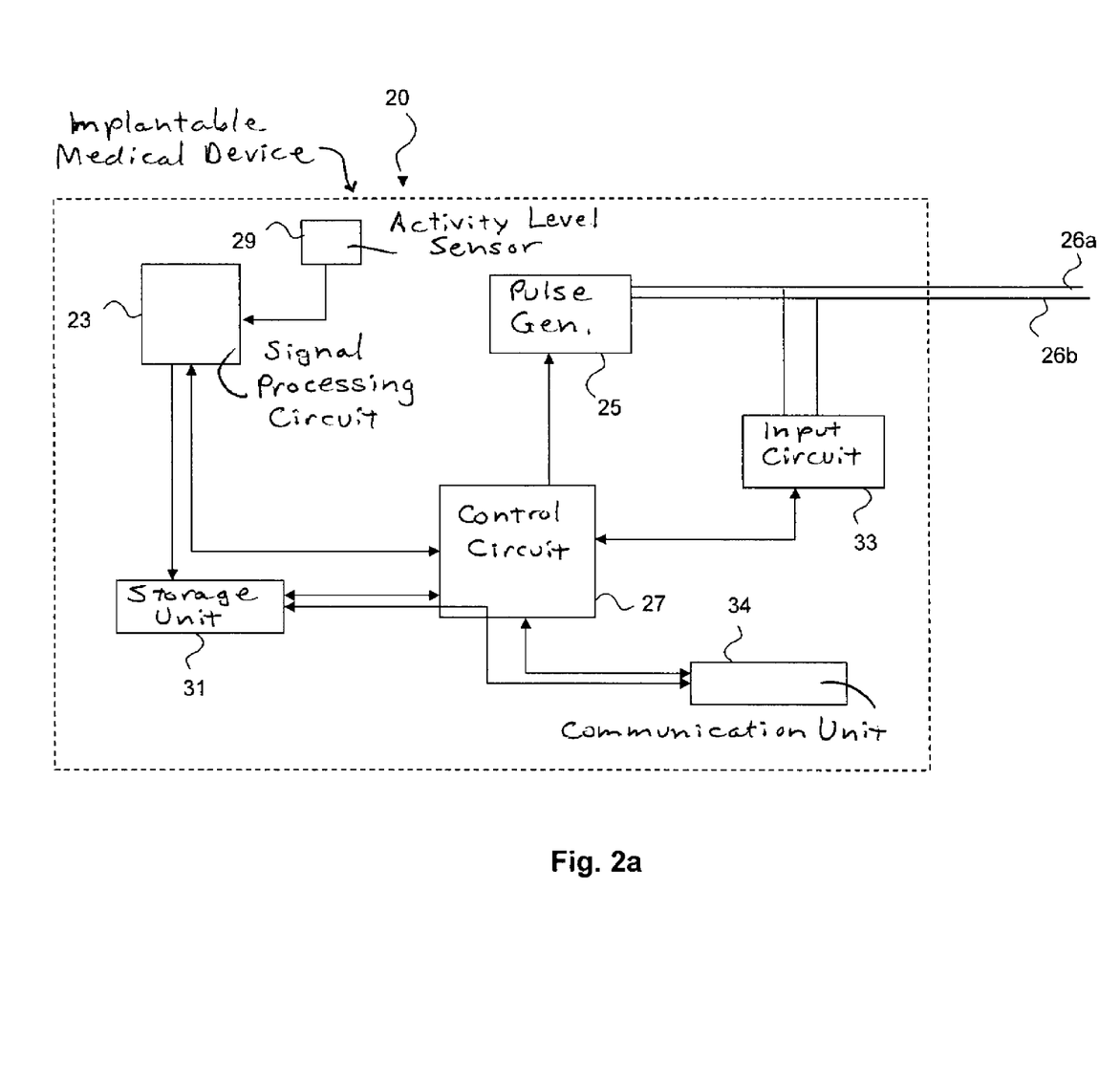
FIG. 2a schematically shows an embodiment of an implantable medical device of the system shown in FIG. 1.
Figure 2B:
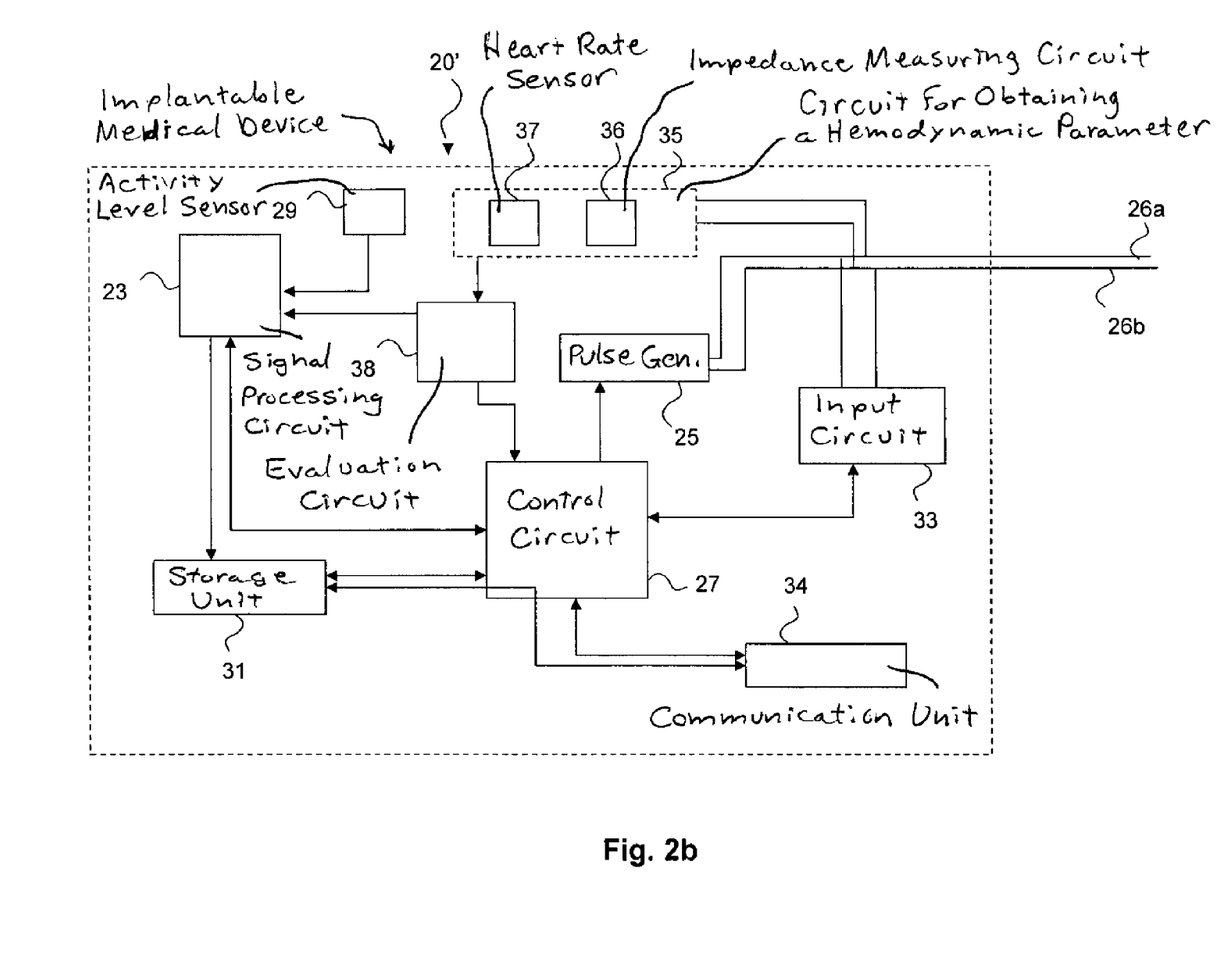
FIG. 2b schematically shows a further embodiment of an implantable medical device of the system shown in FIG. 1.

Turning now to FIGS. 2a and 2b, the configuration including the primary components of embodiments of implantable medical devices of the system 1 described in FIG. 1 will be described.

In FIG. 2a, one embodiment of the implantable medical device according to the present invention is shown. The implantable medical device 20, such as a bi-ventricular pacemaker, has a housing (not shown) being hermetically sealed and biologically inert. Normally, the housing is conductive and may, thus, serve as an electrode. The pacemaker 20 is connectable to one or more pacemaker leads, where only two are shown in FIG. 1; namely a ventricular lead 26a implanted in the right ventricle of the heart (not shown) and one lead 26b implanted in a coronary vein of the left side of the heart (not shown). The leads 26a and 26b can be electrically coupled to the pacemaker 20 in a conventional manner. The leads 26a, 26b carry one or more electrodes, such as a tip electrode or a ring electrode, arranged to, inter alia, measure the impedance or transmit pacing pulses for causing depolarization of cardiac tissue adjacent to the electrode (-s) generated by a pace pulse generator 25 under influence of a controller or controlling circuit 27 including a microprocessor. The controller 27 controls, inter alia, pace pulse parameters such as output voltage and pulse duration.

Furthermore, the implantable medical device 20 includes at least one sensor 29 adapted to sense at least one sensor signal associated with a physiological parameter of the patient. In one embodiment, the sensor 29 is an activity level sensor adapted to sense an activity level of the patient, for example, an accelerometer. The sensor 29 is connected to a signal processing circuit 23 adapted to process sensed signals received from the sensor 29.

Moreover, a storage unit 31 is connected to the controller 27, which storage unit 31 may include a random access memory (RAM) and/or a non-volatile memory such as a read-only memory (ROM). Storage unit 31 is connected to the controller 27 and the signal processing circuit 23. Detected signals from the patient's heart are processed in an input circuit 33 and are forwarded to the controller 27 for use in logic timing determination in known manner. The implantable medical device 20 is powered by a battery (not shown), which supplies electrical power to all electrical active components of the implantable medical device 20. The implantable medical device 20 further has a communication unit 34, for example, an RF telemetry circuitry for providing RF communications. Thereby, for example, data contained in the storage unit 31 can be transferred to a programmer (see FIG. 1) via the communication unit and a programmer interface (not shown) for use in analyzing system conditions, patient information, etc.

In one embodiment, the controller 27 is adapted to obtain at least one sensor value using the sensor signal for each workload level of the stress equipment workload settings during the determination procedure, which will be described in more detail below. Further, the controller 27 is adapted to determine the settings and/or characteristics of the at least one sensor for each workload level using the obtained sensor values.

With reference now to FIG. 2b, another embodiment of an implantable medical device in accordance with the present invention and that can be used in a medical system in accordance with the present invention will be described. Like or similar parts in FIGS. 2a and 2b will be denoted with the same reference numeral and description of parts that have been described with reference to FIG. 2a will be omitted. The implantable medical device 20', such as a bi-ventricular pacemaker, further has a circuit 35 for obtaining a hemodynamical parameter of the heart of the patient. In one embodiment, the circuit 35 has an impedance measuring circuit 36 for measuring an impedance of tissues between right and left side of the heart, which circuit 36 may be connected to the leads 26a and 26b. The impedance may be measured between electrodes placed inside or on the surface of the heart, integrated on a pacemaker lead, for example the leads 26a, 26b. Further, the circuit 35 for obtaining a hemodynamical parameter includes a heart rate sensor 37 for measuring a heart rate of the patient. The heart rate sensor can be incorporated in the device in accordance with conventional practice within the art. Of course, as those skilled in the art will realize, there are other hemodynamical parameters that can be measured, sensed or derived, for example, stroke volume, ejection fraction, heart sounds, blood pressure. As used herein, a hemodynamical parameter encompasses any metric that reflects or relates to actual hemodynamic function.

Moreover, the circuit 35 for obtaining a hemodynamical parameter is adapted to determine a relative cardiac output (CO) based on the measured cardiac impedance and the measured heart rate. A portion of the cardiac impedance carries information of the amount of blood in the left ventricle and thus varies during the heart cycles. The impedance variation during a heart cycle corresponds to stroke volume, i.e. the volume of blood ejected per heart beat and equals end-diastolic volume minus end-systolic value. This portion of the measured impedance or impedance information is extracted in the impedance measuring circuit 36 or the circuit 35 for obtaining a hemodynamical parameter. Thereby, the circuit 35 for obtaining a hemodynamical parameter may obtain a relative value of the cardiac output, i.e. by knowing the heart rate and a relative value of the stroke volume of the left ventricle. The cardiac output is the volume of blood, measured in liters, ejected by the heart per minute and is determined by multiplying the heart rate and the stroke volume. Accordingly, the value of the cardiac output obtained by the circuit 35 for obtaining a hemodynamical parameter is a relative value.

Furthermore, the implantable medical device 20' has an evaluation circuit 38 adapted to evaluate the obtained hemodynamical parameter (in one embodiment the cardiac output), the sensor signal (in one embodiment the activity level of the patient) and workload data for each workload level of the stress equipment workload settings, which may be stored in the memory circuit 31 of the implantable device 20' or in the programmer 2 (see FIG. 1), in which case the stress equipment workload settings can be obtained by the implantable device by means of a data transfer using the communication unit 34.

In one embodiment, the evaluation circuit 38 is adapted to evaluate the at least one hemodynamical parameter, e.g. a relative value of the cardiac output as described above, and the workload data for each workload level of the stress equipment workload settings. Further, the controller 27 may be adapted to iteratively control a delivery of the pacing pulses based on the evaluation and to determine optimal pacing settings for each workload level of the stress equipment workload settings. In addition, the evaluation circuit 38 may be adapted use at least one sensor signal from a sensor, wherein the at least one sensor is an activity level sensor adapted to sense an activity level of the patient, for each workload level of the stress equipment workload settings during the determination procedure in the evaluation.

Figure 3:
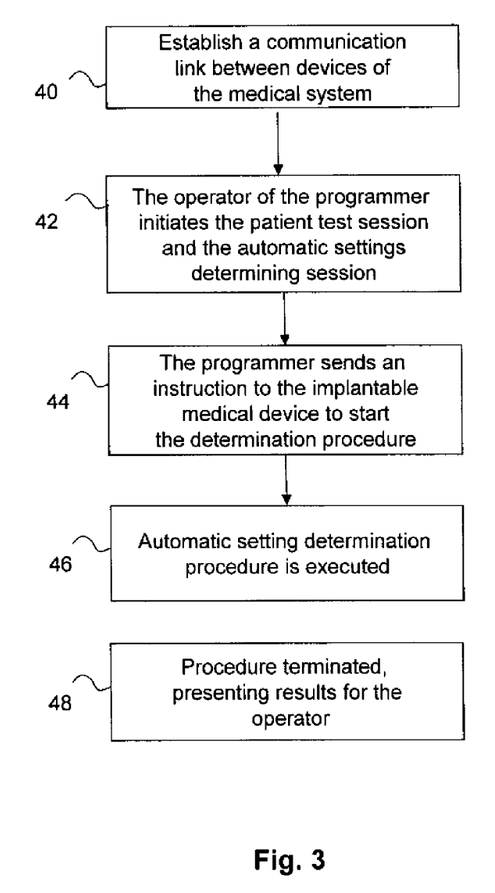
FIG. 3 is a high-level flow chart of the methods for setting or characterizing a sensor of the implantable medical device or for optimizing a pacing setting of an implantable medical device according to the present invention.

With reference now to FIG. 3, a high-level description of the steps of the methods for setting or characterizing a sensor of the implantable medical device or for optimizing a pacing setting of an implantable medical device according to the present invention will be given. First, in step 40, a communication link between the devices of a medical system, e.g. the devices of the system 1 in FIG. 1, is established. For example, this can be performed by an operator of the programmer, e.g. a physician, using the input devices of the programmer 2. Thereafter, at step 42, the operator of the programmer initiates the patient test session and the automatic setting determination procedure, e.g. for characterizing the activity sensor of the implantable medical device 20 or for determining a pacing setting of the implantable medical device 20 such as a VV-delay. Subsequently, at step 44, the programmer 2 sends a command or instruction to the implantable medical device to initiate the automatic setting determination procedure. Then, at step 46, the automatic setting determination procedure is initiated and executed as will be described in detail hereinafter. Finally, at step 48, the operator of the programmer is presented for a message, e.g. on the display unit informing the operator of the finalization of the automatic setting determination procedure.

Figure 4:
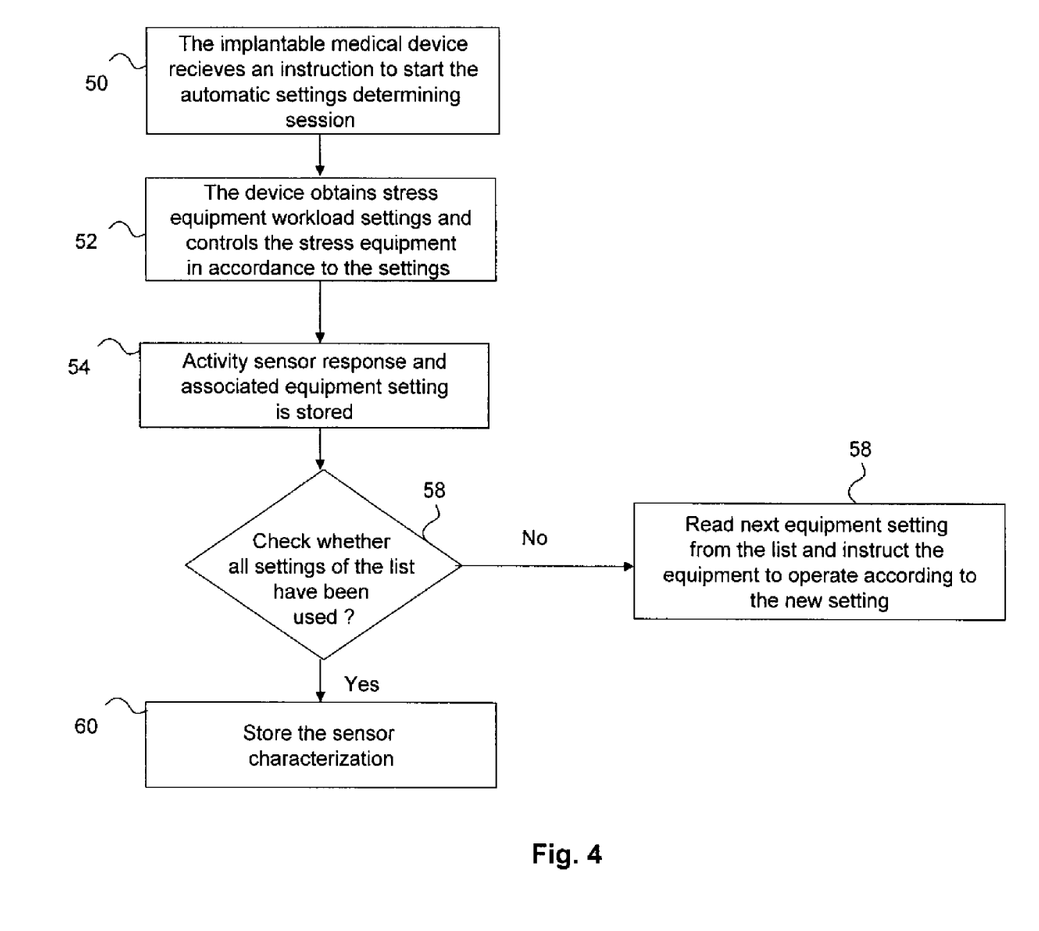
FIG. 4 is a flow chart of a procedure for determining settings of a sensor or characterizing a sensor of the implantable medical device in accordance with the present invention.

Referring to FIG. 4, a procedure for determining settings of a sensor or characterizing a sensor of the implantable medical device 20 will be described. First, at step 50, the implantable medical device 20 receives an instruction to start the automatic setting determination procedure from the programmer. That is, after the communication link between the devices of a medical system, e.g. the devices of the system 1 in FIG. 1, has been established the patient test session and the automatic setting determination procedure have been initiated by the operator of the programmer 2. Then, at step 52, the controller 27 of the device 20 obtains a stress equipment workload setting list, which can be stored in the memory circuit 31 or in the memory circuit 7 of the programmer 2 and the device 20 sends an instruction to the stress equipment 6 to start operate at an initial workload, for example, at zero workload. Thus, the patient is exterted for an initial exertion or stress, for example, on a treadmill. The stress equipment workload setting list may be a predetermined protocol for the patient including a sequence of workload level settings, i.a. equipment speed, equipment inclination in case of a treadmill and the duration of each workload level setting. The controller 27 of the device 20 may control the stress equipment in accordance with the predetermined workload setting or the protocol including the predetermined setting may be transferred to the stress equipment. At step 54, the activity sensor response a predetermined time after a new equipment setting is stored and associated with the present equipment setting. Then, at step 56, it is checked whether all equipment settings of the list have been used. If no, the procedure returns to step 58 and the next equipment setting is read from the list and the stress equipment is instructed to adjust the workload in accordance to the new settings. On the other hand, if all settings of the list have been used, the procedure proceeds to step 60 where all sensor responses and corresponding stress equipment settings, i.e. the sensor characterization (measured sensor signal vs. stress equipment setting) is stored in the memory circuit 31 of the implantable medical device 20. Thereafter, a stop command is sent to the stress equipment 6 and to the programmer 2 informing them that the procedure is completed. The operator, e.g. a physician, may be informed of the results from the characterization procedure on the display unit via the graphical user interface of the programmer 2.

Figure 5:
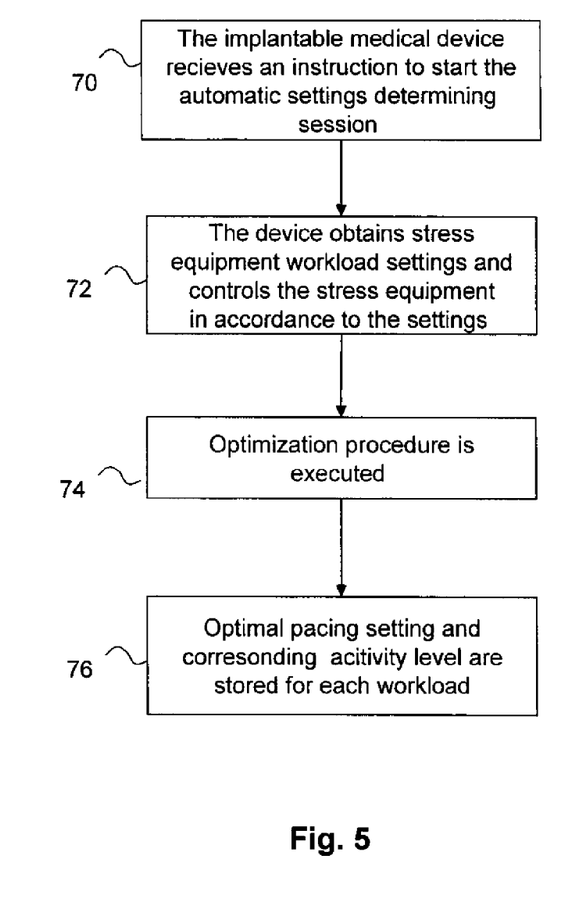
FIG. 5 is a flow chart describing an algorithm for determining or optimizing a VV-delay of an implantable medical device in accordance with the present invention.

Turning now to FIG. 5, an algorithm for determining or optimizing a pacing setting such as a VV-delay of an implantable medical device will be described. First, at step 70, the implantable medical device 20 receives an instruction to start the automatic setting determination procedure from the programmer 2. That is, after the communication link between the units and/or devices of a medical system, e.g. the devices of the system 1 or 1' in FIGS. 1a and 1b, respectively, has been established, the patient test session and the automatic setting determination procedure have been initiated by the operator of the programmer 2, the implantable medical device 20 receives the instruction to start the automatic setting determination procedure from the programmer 2. Then, at step 72, the controller 27 of the device 20 obtains a stress equipment workload setting list, which can be stored in the memory circuit 31 or in the memory circuit 7 of the programmer 2 and the device 20 sends an instruction to the stress equipment 6 to start operate at an initial workload, for example, at zero workload. Thus, the patient is exterted for a initial stress, for example, on a treadmill. The stress equipment workload setting list may be a predetermined protocol for the patient including a sequence of workload level settings, i.a. equipment speed, equipment inclination in case of a treadmill and the duration of each workload level setting. The controller 27 of the device 20 may control the stress equipment in accordance with the predetermined workload setting or the protocol including the predetermined setting may be transferred to the stress equipment.

Subsequently, at step 74, an optimization of the pacing settings of the device, for example, the VV-delay at the current workload is performed or executed. The optimization procedure will be described in more detail with reference to FIG. 6. Thereafter, at step 76, the optimal VV-delay and the corresponding sensor value, i.e. in this embodiment the activity level, are returned from the optimization subroutine and are stored. This is repeated for the sequence of workloads of the list and, hence, a matrix of optimal VV-delays and corresponding activity levels are created and stored, for example, in the memory circuit 31 of the implantable medical device 20. Then, the automatic setting determination procedure is terminated and the operator may be presented for the results on the display unit of the programmer 2.

Figure 6:
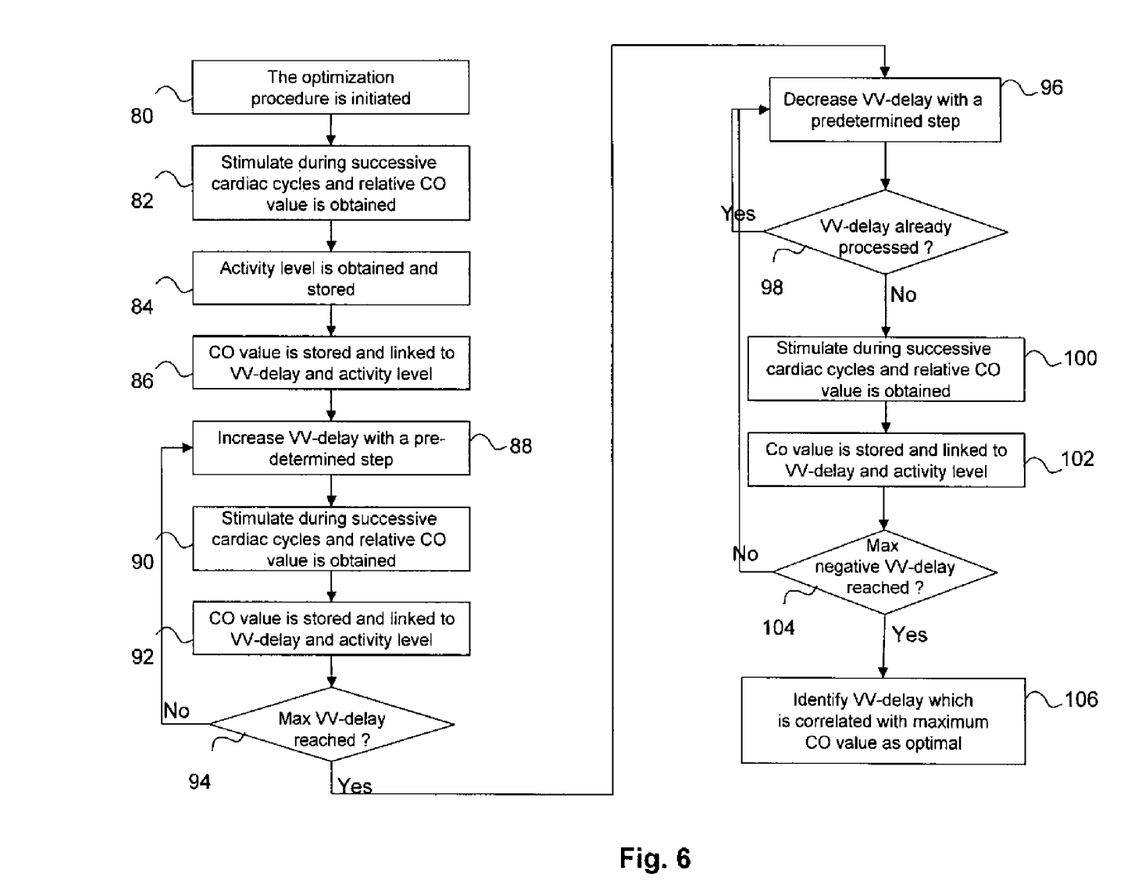
FIG. 6 is a flow chart showing the optimization procedure according to the present invention shown in FIG. 5 in more detail.

Referring now to FIG. 6, the optimization procedure according to the present invention will be described in detail. The procedure is described with reference to an optimization of a VV-delay but, however, as the skilled person realizes, the present optimization procedure may also be performed to optimize other pacing settings of an implantable medical device, such as, the AV-delay.

First, at step 80, an initialization is executed, the VV-delay is set to zero and the stress equipment is instructed to operate according to the workload settings list, i.e. equipment speed and inclination is set according to the list in case of a treadmill. The controller 27 of the implantable medical device 20 may be adapted to obtain a VV-delay optimization protocol including the initial or start VV-delay, the increments or step increase to use during the optimization, maximum VV-delay, maximum negative VV-delay, and step decrease to use during the optimization. This protocol may be stored in the memory circuit 31 of the implantable device or it may be obtained or transferred from the programmer workstation 2 at initialization of the optimization procedure.

Then, at step 82, the heart is stimulated bi-ventricularly during a number of successive cardiac cycles and a relative value of the cardiac output (CO) is obtained in accordance with the description given above. At step 84, the activity level is obtained from the activity sensor (or sensors) and stored. As the skilled person realizes, there are other conceivable physiological parameters that can be used instead of, or as a complement to the activity level to improve the optimization, for example, the posture of the patient or the breath rate of the patient.

At step 86, the obtained CO-value is stored and linked to the present VV-delay and the obtained activity level. Subsequently, at step 88, the VV-delay is increased with a predetermined step in accordance with the VV-delay protocol. At step 90, the heart is stimulated bi-ventricularly during a number of successive cardiac cycles and a relative value of the cardiac output (CO) is obtained in accordance with the description given above. Then, at step 92, the obtained CO-value is stored and linked to the present VV-delay and the obtained activity level. Thereafter, at step 94, it is checked whether the maximal VV-delay has been reached. If no, the algorithm returns to step 88 and, on the other hand, if yes, the algorithm proceeds to step 96 where the VV-delay is decreased with a predetermined step. Thereafter, at step 98, it is checked if the present VV-delay already has been processed. If yes, the algorithm returns to the previous step, step 98, and the VV-delay is decreased yet another step. If it is verified in step 96 that the present VV-delay not has been processed, the algorithm proceeds to step 100 where the heart is stimulated bi-ventricularly during a number of successive cardiac cycles and a relative value of the cardiac output (CO) is obtained in accordance with the description given above. Subsequently, at step 102, the obtained CO-value is stored and linked to the present VV-delay and the obtained patient activity level. After this, at step 104, it is checked whether the maximum negative VV-delay has been reached. If no, the algorithm returns to step 96 and the present VV-delay is decreased with a predetermined step. If it is verified that the maximum negative VV-delay has been reached, the algorithm instead proceeds to step 106 where the VV-delay which is correlated with the maximum CO value is identified and stored as the optimal VV-delay for the present activity level.

According to another embodiment of the present invention, the controller 27 of the implantable medical device is adapted to supervise the condition of the patient undergoing the patient test session at the stress equipment. This can be performed, for example, by monitoring or observing the cardiac output (CO) and the patient activity levels. In case of worsening of the condition, e.g. if the cardiac output is found to exceed or fall below predetermined limits, the controller may be adapted to, for example, reduce the speed or inclination of the stress equipment and thus reduce the workload of the patient. Thereby, the safety of the patient can be enhanced during the test sessions.

Although modifications and changes may be suggested by those skilled in the art, it is the intention of the inventors to embody within the patent warranted heron all changes and modifications as reasonably and properly come within the scope of their contribution to the art.

The invention claimed is:

1. A medical system comprising:
an intracorporeally implantable medical device containing a pulse generator configured to emit cardiac stimulation pulses for pacing the heart of the patient, a control unit that controls operation of said pulse generator according to settings of said control unit, and an implantable device communication unit connected at least to said control unit;
an extracorporeal programmer comprising a programmer control unit and a programmer communication unit;
extracorporeal stress equipment configured to interact with said patient to exert a physiological stress on said patient according to predetermined stress equipment workload settings, and a stress equipment communication unit that communicates with said programmer communication unit;
said control unit of said programmer being configured to start a patient test session, including initiating an automatic setting determination procedure to set said stress equipment workload settings, by starting operation of said stress equipment;
said control unit of said programmer being configured to communicate said predetermined stress equipment workload settings to said control unit of said implantable medical device via said implantable device communication unit and said programmer communication unit;
said implantable medical device further comprising a sensor configured to interact with the patient to generate a sensor signal representing a physiological parameter of the patient that is influenced by said stress equipment; and
said control unit of said implantable medical device being configured to identify a characteristic of said sensor value for each workload setting.

2. A system as claimed in claim 1 wherein said sensor is an activity level sensor that senses an activity level of the patient.

3. A system as claimed in claim 1 wherein said implantable medical device further comprises a memory configured to store said characteristic of said sensor value for each workload setting.

4. A system as claimed in claim 1 wherein said control unit of said programmer is configured, upon receiving a patient test session initiation command, to establish a communication link between said programmer and said implantable medical device and said stress equipment via said implantable device communication unit, said programmer communication unit, and said stress equipment communication unit that enables bi-directional communications between said programmer and said stress equipment and said stress equipment and said programmer and said implantable medical device.

5. A system as claimed in claim 4 wherein said control unit of said programmer is configured, after establishing said communication link to said implantable medical device, to send an initiation command to said control unit of said implantable medical device that initiates said automatic determination procedure in said implantable medical device.

6. A system as claimed in claim 1 wherein said control unit of said implantable medical device is configured to generate a list of stress equipment workload settings for a predetermined number of different workload levels, and to send running instructions to said extracorporeal stress equipment that instruct said extracorporeal stress equipment to operate according to said stress equipment workload settings of said list.

7. A system as claimed in claim 6 wherein said control unit of said implantable medical device is configured to store said workload setting list in a memory of said implantable medical device as a predetermined protocol.

8. A system as claimed in claim 1 wherein said implantable medical device comprises a signal processing unit configured to process said sensor signal, and to start a signal processing procedure wherein said sensor signal is processed, at a predetermined time duration following a change of a workload level according to said workload settings.

9. A system as claimed in claim 1 wherein said implantable medical device further comprises a circuit configured to obtain a hemodynamic parameter of the heart of the patient during successive cardiac cycles for each workload level of said stress equipment workload settings, and evaluation circuit configured to evaluate said hemodynamic parameter and said sensor signal and said workload level for each workload of said stress equipment workload settings to obtain an evaluation result, and wherein said control unit of said implantable medical device is configured to iteratively control delivery of said pacing pulses by said pulse generator based on said evaluation result at optimized pacing settings for each workload level of said stress equipment workload settings.

10. A system as claimed in claim 9 wherein said circuit for obtaining a hemodynamic parameter comprises a circuit configured to measure impedance of tissue between a right side of the heart and a left side of the heart for successive cardiac cycles, and a circuit for measuring a heart rate of the patient, and wherein said circuit for obtaining a hemodynamic parameter is configured to determine a relative cardiac output based on the measured impedance and the measured heart rate for successive cardiac cycles.

11. A system as claimed in claim 9 wherein said control circuit of said implantable medical device is configured to (a) select an initial workload setting from among said predetermined stress equipment workload settings, (b) operate said stress equipment according to the selected workload setting via said medical device communication unit and said stress equipment communication unit, (c) iteratively controlled delivery of pacing pulses by said pulse generator based on said evaluation result, (d) determine optimal pacing settings for an initial workload level, (e) store said optimal pacing settings and a corresponding activity level for said initial workload level in a memory in said implantable medical device, (f) repeat (b), (c), (d) and (e) for each workload level of said stress equipment workload setting, in place of said initial workload setting, and (g) store a matrix of pacing settings and corresponding activity levels in said memory.

12. A system as claimed in claim 9 wherein said control unit of said implantable medical device sets VV-delay settings as said optimal pacing settings.

13. A medical system comprising:
an intracorporeally implantable medical device containing a pulse generator configured to emit cardiac stimulation pulses for pacing the heart of the patient at different pacing settings, a control circuit that controls operation of said pulse generator according to settings of said control unit, and an implantable device communication unit connected at least to said control unit;
an extracorporeal programmer comprising a programmer control unit and a programmer communication unit;
extracorporeal stress equipment configured to interact with said patient to exert a physiological stress on said patient according to predetermined stress equipment workload settings, and a stress equipment communication unit that communicates with said programmer communication unit;
said control unit of said programmer being configured to start a patient test session, including initiating an automatic setting determination procedure to set said stress equipment workload settings, by starting operation of said stress equipment;
said control unit of said programmer being configured to communicate said predetermined stress equipment workload settings to said control unit of said implantable medical device via said medical device communication unit and said programmer communication unit;
said implantable medical device further comprising a circuit configured to interact with the patient to detect, for each workload setting a hemodynamic parameter of the patient that is influenced by said stress equipment, and an evaluation circuit configured to evaluate said hemodynamic parameter and said workload setting for each workload setting made to obtain an evaluation result; and
said control circuit of said implantable medical device being configured to iteratively control delivery of said stimulation pulses by said pulse generator by selecting optimal pacing settings dependent on said evaluation result.

14. A system as claimed in claim 13 wherein said implantable medical device further comprises a sensor configured to interact with the patient to generate a sensor signal representing a physiological parameter of the patient that is influenced by said stress equipment, and wherein said control unit of said implantable medical device is configured to identify a characteristic of said sensor value for each workload setting.

15. A system as claimed in claim 14 wherein said sensor is an activity level sensor that senses an activity level of the patient.

16. A system as claimed in claim 15 wherein said implantable medical device further comprises a memory configured to store said characteristic of said sensor value for each workload setting.

17. A system as claimed in claim 13 wherein said control unit of said programmer is configured, upon receiving a patient test session initiation command, to establish a communication link between said programmer and said implantable medical device and said stress equipment via said medical device communication unit, said programmer communication unit, and said stress equipment communication unit that enables bi-directional communications between said programmer and said stress equipment and said stress equipment and said programmer and said implantable medical device.

18. A system as claimed in claim 17 wherein said control unit of said programmer is configured, after establishing said communication link to said implantable medical device, to send an initiation command to said control unit of said implantable medical device that initiates said automatic determination procedure in said implantable medical device.

19. A system as claimed in claim 13 wherein said control unit of said implantable medical device is configured to generate a list of stress equipment workload settings for a predetermined number of different workload settings, and to send running instructions to said extracorporeal stress equipment that instruct said extracorporeal stress equipment to operate according to said stress equipment workload settings of said list.

20. A system as claimed in claim 19 wherein said control unit of said implantable medical device is configured to store said workload setting list in a memory of said implantable medical device as a predetermined protocol.

21. A system as claimed in claim 13 wherein said implantable medical device comprises a signal processing unit configured to process said sensor signal, and to start a signal processing procedure wherein said sensor signal is processed, at a predetermined time duration following a change of said workload setting according to said workload settings.

22. A system as claimed in claim 13 wherein said circuit for obtaining a hemodynamic parameter comprises a circuit configured to measure impedance of tissue between a right side of the heart and a left side of the heart for successive cardiac cycles, and a circuit for measuring a heart rate of the patient, and wherein said circuit for obtaining a hemodynamic parameter is configured to determine a relative cardiac output based on the measured impedance and the measured heart rate for successive cardiac cycles.

23. A system as claimed in claim 13 wherein said control circuit of said implantable medical device is configured to (a) select an initial workload setting from among said predetermined stress equipment workload settings, (b) operate said stress equipment according to the selected workload setting via said medical device communication unit and said stress equipment communication unit, (c) iteratively controlled delivery of pacing pulses by said pulse generator based on said evaluation result, (d) determine optimal pacing settings for an initial workload level, (e) store said optimal pacing settings and a corresponding activity level for said initial workload level in a memory in said implantable medical device, (f) repeat (b), (c), (d) and (e) for each workload level of said stress equipment workload setting, in place of said initial workload setting, and (g) store a matrix of pacing settings and corresponding activity levels in said memory.

24. A system as claimed in claim 13 wherein said control unit of said implantable medical device sets VV-delay settings as said optimal pacing settings.

25. A system as claimed in claim 13 further comprising extracorporeal diagnostic equipment configured to interact with the patient to obtain a diagnostic result therefrom, said extracorporeal diagnostic equipment including a diagnostic equipment communication unit configured for bi-directional communication with at least one of said programmer communication unit, said medical device communication unit and said stress equipment communication unit, said diagnostic equipment being configured to measure a physiological parameter of the patient used in said automatic setting determination procedure.

26. A system as claimed in claim 25 wherein said external diagnostic equipment is an ultrasound unit that obtains an ultrasound image of the patient.

27. A method for operating a medical system comprising an intracorporeally implantable medical device containing a pulse generator configured to emit cardiac stimulation pulses for pacing the heart of the patient, a control unit that controls operation of said pulse generator according to settings of said control unit, and an implantable device communication unit connected at least to said control unit, an extracorporeal programmer comprising a programmer control unit and a programmer communication unit, and extracorporeal stress equipment configured to interact with said patient to exert a physiological stress on said patient according to predetermined stress equipment workload settings, and a stress equipment communication unit that communicates with said programmer communication unit, said method comprising the steps of:

from said control unit of said programmer, starting a patient test session, including initiating an automatic setting determination procedure to set said stress equipment workload settings, by starting operation of said stress equipment;

from said control unit of said programmer, communicating said predetermined stress equipment workload settings to said control unit of said implantable medical device via said implantable device communication unit and said programmer communication unit;

with a sensor in said implantable medical device, interacting with the patient to generate a sensor signal representing a physiological parameter of the patient that is influenced by said stress equipment; and from said control unit of said implantable medical device, iteratively controlling delivery of said stimulation pulses by said pulse generator by selecting optimal pacing settings dependent on said evaluation result.

28. A method as claimed in claim 27 comprising, as said sensor, employing an activity level sensor that senses an activity level of the patient.

29. A method as claimed in claim 27 comprising, in a memory in said implantable medical device, storing a characteristic of said sensor value for each workload setting.

30. A method as claimed in claim 27 comprising, upon said control unit of said programmer receiving a patient test session initiation command, establishing a communication link between said programmer and said implantable medical device and said stress equipment via said implantable device communication unit, said programmer communication unit, and said stress equipment communication unit that enables bi-directional communications between said programmer and said stress equipment and said stress equipment and said programmer and said implantable medical device.

31. A method as claimed in claim 30 comprising, from said control unit of said programmer, after establishing said communication link to said implantable medical device, sending an initiation command to said control unit of said implantable medical device that initiates said automatic determination procedure in said implantable medical device.

32. A method as claimed in claim 27 comprising, in said control unit of said implantable medical device, generating a list of stress equipment workload settings for a predetermined number of different workload settings, and sending running instructions from said control unit of said implantable medical device to said extracorporeal stress equipment that instruct said extracorporeal stress equipment to operate according to said stress equipment workload settings of said list.

33. A method as claimed in claim 27 comprising, from said control unit of said implantable medical device, storing said workload setting list in a memory of said implantable medical device as a predetermined protocol.

34. A method as claimed in claim 27 wherein said implantable medical device comprises a signal processing unit configured to process said sensor signal, and comprising starting a signal processing procedure wherein said sensor signal is processed, at a predetermined time duration following a change of said workload setting according to said workload settings.

35. A method as claimed in claim 27 comprising, via a circuit in said implantable medical device, obtaining a hemodynamic parameter of the heart of the patient during successive cardiac cycles for each workload setting of said stress equipment workload settings, and, in an evaluation circuit in said implantable medical device, evaluating said hemodynamic parameter and said sensor signal and said workload setting for each workload of said stress equipment workload settings to obtain an evaluation result, and in said control unit of said implantable medical device, iteratively controlling delivery of said pacing pulses by said pulse generator based on said evaluation result at optimized pacing settings for each workload setting of said stress equipment workload settings.

36. A method as claimed in claim 35 comprising obtaining said hemodynamic parameter by measuring impedance of tissue between a right side of the heart and a left side of the heart for successive cardiac cycles, and measuring a heart rate of the patient, and obtaining said hemodynamic parameter by determining a relative cardiac output based on the measured impedance and the measured heart rate for successive cardiac cycles.

37. A method as claimed in claim 35 comprising, in said control circuit of said implantable medical device to (a) selecting an initial workload setting from among said predetermined stress equipment workload settings, (b) operating said stress equipment according to the selected workload setting via said medical device communication unit and said stress equipment communication unit, (c) iteratively controlling delivery of pacing pulses by said pulse generator based on said evaluation result, (d) determining optimal pacing settings for an initial workload level, (e) storing said optimal pacing settings and a corresponding activity level for said initial workload level in a memory in said implantable medical device, (f) repeating (b), (c), (d) and (e) for each workload level of said stress equipment workload setting, in place of said initial workload setting, and (g) storing a matrix of pacing settings and corresponding activity levels in said memory.

38. A method as claimed in claim 27 comprising, from said control unit of said implantable medical device, setting VV-delay settings as said optimal pacing settings.

39. A method for operating a medical system comprising an intracorporeally implantable medical device containing a pulse generator configured to emit cardiac stimulation pulses for pacing the heart of the patient, a control unit that controls operation of said pulse generator according to settings of said control unit, and an implantable device communication unit connected at least to said control unit, an extracorporeal programmer comprising a programmer control unit and a programmer communication unit, and extracorporeal stress equipment configured to interact with said patient to exert a physiological stress on said patient according to predetermined stress equipment workload settings, and a stress equipment communication unit that communicates with said programmer communication unit, said method comprising the steps of:
from said control unit of said programmer, starting a patient test session, including initiating an automatic setting determination procedure to set said stress equipment workload settings, by starting operation of said stress equipment;
from said control unit of said programmer, communicating said predetermined stress equipment workload settings to said control units of said implantable medical device via said medical device communication unit and said programmer communication unit;
via a circuit in said implantable medical device, interacting with the patient to detect, for each workload setting a hemodynamic parameter of the patient that is influenced by said stress equipment and, in an evaluation circuit in said implantable medial device, evaluating said hemodynamic parameter and said workload setting for each workload setting made to obtain an evaluation result; and
from said control circuit of said implantable medical device, identifying a setting or characteristic of said sensor value for each workload setting.

40. A method as claimed in claim 39 comprising, with a sensor in said implantable medical device, interacting with the patient to generate a sensor signal representing a physiological parameter of the patient that is influenced by said stress equipment, said control unit of said implantable medical device, identifying a characteristic of said sensor value for each workload setting.

41. A method as claimed in claim 40 comprising, as said sensor, employing an activity level sensor that senses an activity level of the patient.

42. A method as claimed in claim 40 comprising, in a memory in said implantable medical device, storing said characteristic of said sensor value for each workload setting.

43. A method as claimed in claim 39 comprising, upon said control unit of said programmer receiving a patient test session initiation command, establishing a communication link between said programmer and said implantable medical device and said stress equipment via said implantable device communication unit, said programmer communication unit, and said stress equipment communication unit that enables bi-directional communications between said programmer and said stress equipment and said stress equipment and said programmer and said implantable medical device.

44. A method as claimed in claim 43 comprising, from said control unit of said programmer, after establishing said communication link to said implantable medical device, sending an initiation command to said control unit of said implantable medical device that initiates said automatic determination procedure in said implantable medical device.

45. A method as claimed in claim 39 comprising, in said control unit of said implantable medical device, generating a list of stress equipment workload settings for a predetermined number of different workload levels, and sending running instructions from said control unit of said implantable medical device to said extracorporeal stress equipment that instruct said extracorporeal stress equipment to operate according to said stress equipment workload settings of said list.

46. A method as claimed in claim 15 comprising, from said control unit of said implantable medical device, storing said workload setting list in a memory of said implantable medical device as a predetermined protocol.

47. A method as claimed in claim 39 wherein said implantable medical device comprises a signal processing unit configured to process said sensor signal, and comprising starting a signal processing procedure wherein said sensor signal is processed, at a predetermined time duration following a change of said workload setting according to said workload settings.

48. A method as claimed in claim 39 comprising obtaining said hemodynamic parameter by measuring impedance of tissue between a right side of the heart and a left side of the heart for successive cardiac cycles, and measuring a heart rate of the patient, and obtaining said hemodynamic parameter by determining a relative cardiac output based on the measured impedance and the measured heart rate for successive cardiac cycles.

49. A method as claimed in claim 39 comprising, in said control circuit of said implantable medical device to (a) selecting an initial workload setting from among said predetermined stress equipment workload settings, (b) operating said stress equipment according to the selected workload setting via said medical device communication unit and said stress equipment communication unit, (c) iteratively controlling delivery of pacing pulses by said pulse generator based on said evaluation result, (d) determining optimal pacing settings for an initial workload level, (e) storing said optimal pacing settings and a corresponding activity level for said initial workload level in a memory in said implantable medical device, (f) repeating (b), (c), (d) and (e) for each workload level of said stress equipment workload setting, in place of said initial workload setting, and (g) storing a matrix of pacing settings and corresponding activity levels in said memory.

50. A method as claimed in claim 39 comprising, from said control unit of said implantable medical device, setting VV-delay settings as said optimal pacing settings.

51. A method as claimed in claim 39 comprising using extracorporeal diagnostic equipment configured to interact with the patient to obtain a diagnostic result therefrom, said extracorporeal diagnostic equipment including a diagnostic equipment communication unit configured for bi-directional communication with at least one of said programmer communication unit, and with said medical device communication unit and said stress equipment communication unit, said diagnostic equipment, measuring a physiological parameter of the patient used in said automatic setting determination procedure.

52. A method as claimed in claim 51 comprising employing as, said external diagnostic equipment, an ultrasound unit and obtaining an ultrasound image of the patient.

* * * * *